(12) United States Patent
Karkouche

(10) Patent No.: US 11,187,631 B2
(45) Date of Patent: Nov. 30, 2021

(54) DEVICE FOR CAPTURING BIOLOGICAL PARTICLES

(71) Applicant: KABCYT, Antony (FR)

(72) Inventor: Bastien Karkouche, Antony (FR)

(73) Assignee: KABCYT, Antony (FR)

( * ) Notice: Subject to any disclaimer, the term of this patent is extended or adjusted under 35 U.S.C. 154(b) by 337 days.

(21) Appl. No.: 16/333,430

(22) PCT Filed: Sep. 20, 2017

(86) PCT No.: PCT/EP2017/073749
§ 371 (c)(1),
(2) Date: Mar. 14, 2019

(87) PCT Pub. No.: WO2018/054961
PCT Pub. Date: Mar. 29, 2018

(65) Prior Publication Data
US 2019/0250082 A1    Aug. 15, 2019

(30) Foreign Application Priority Data

Sep. 20, 2016 (FR) ...................................... 1658828

(51) Int. Cl.
*G01N 1/40* (2006.01)
*B01L 3/00* (2006.01)
(Continued)

(52) U.S. Cl.
CPC .............. *G01N 1/4077* (2013.01); *B01L 3/00* (2013.01); *B01L 3/502* (2013.01); *B01L 9/06* (2013.01);
(Continued)

(58) Field of Classification Search
CPC .. G01N 1/4077; G01N 35/1065; G01N 1/405; G01N 2001/4088; G01N 1/2813;
(Continued)

(56) References Cited

U.S. PATENT DOCUMENTS 4,921,615 A * 5/1990 Lindoerfer ............. C12M 47/02
210/729
5,905,038 A * 5/1999 Parton .................... C12M 33/14
435/287.6
(Continued)

FOREIGN PATENT DOCUMENTS

CA    2347004 A1 *  4/2000  ............... C12Q 1/24
DE   19608372 A1     9/1997
(Continued)

OTHER PUBLICATIONS

International Search Report corresponding International application PCT/EP2017/073749 dated Dec. 8, 2017, 3 pages.

*Primary Examiner* — Jill A Warden
*Assistant Examiner* — Henry H Nguyen
(74) *Attorney, Agent, or Firm* — Cooper Legal Group, LLC; Ronald M. Kachmarik

(57) ABSTRACT

A device for capturing biological particles in suspension in a liquid medium. The device includes a container that is open via a lower opening, and a filter membrane fixed on the container in such a way as to close the lower opening. Inside the container are: a buffer made of a porous foam and having a planar face resting on the filter membrane, an absorbent block resting on the buffer and able to absorb the liquid medium when it is in contact with the liquid medium, and a spring designed to impede the expansion and/or movement of the absorbent block away from the lower opening of the container. Also, methods for capturing biological particles in suspension in a liquid medium using a capture device, and preparation a sample intended for biological analysis. Further an analysis apparatus that has a capture device.

17 Claims, 4 Drawing Sheets

(51) Int. Cl.
*G01N 35/10* (2006.01)
*B01L 9/06* (2006.01)
*C12M 1/26* (2006.01)
*C12M 1/00* (2006.01)
*G01N 1/28* (2006.01)

(52) U.S. Cl.
CPC .............. *C12M 1/26* (2013.01); *C12M 33/04* (2013.01); *C12M 47/02* (2013.01); *C12M 47/04* (2013.01); *G01N 1/28* (2013.01); *G01N 1/405* (2013.01); *G01N 35/10* (2013.01); *G01N 35/1065* (2013.01); *B01L 2300/069* (2013.01); *B01L 2300/0681* (2013.01); *B01L 2300/0832* (2013.01); *B01L 2300/123* (2013.01); *B01L 2400/0478* (2013.01); *C12M 33/14* (2013.01); *G01N 2001/2826* (2013.01); *G01N 2001/4088* (2013.01)

(58) Field of Classification Search
CPC .. G01N 35/10; G01N 1/40; G01N 2001/2826; B01L 9/06; B01L 3/502; B01L 2300/069; B01L 2300/123; B01L 2300/0832; B01L 2400/0478; B01L 2300/0681; B01L 3/00; C12M 33/04; C12M 47/02; C12M 47/04; C12M 33/14; C12M 1/00; C12M 1/26
See application file for complete search history.

(56) References Cited

U.S. PATENT DOCUMENTS

| 2002/0106718 | A1 | 8/2002 | Gombrich et al. |
| 2008/0142456 | A1 | 6/2008 | Duhamel et al. |
| 2010/0326214 | A1* | 12/2010 | Hornes .................. B01L 3/021 73/864.01 |
| 2011/0074451 | A1* | 3/2011 | Yamaguchi ........ G01N 15/1031 324/693 |
| 2011/0123977 | A1* | 5/2011 | Sprenkels ............. B01L 3/0255 435/5 |
| 2011/0159533 | A1* | 6/2011 | Karkouche ............ C12M 47/02 435/29 |

FOREIGN PATENT DOCUMENTS

| EP | 1972945 A1 | 9/2008 |
| WO | 2010012941 A2 | 2/2010 |

\* cited by examiner

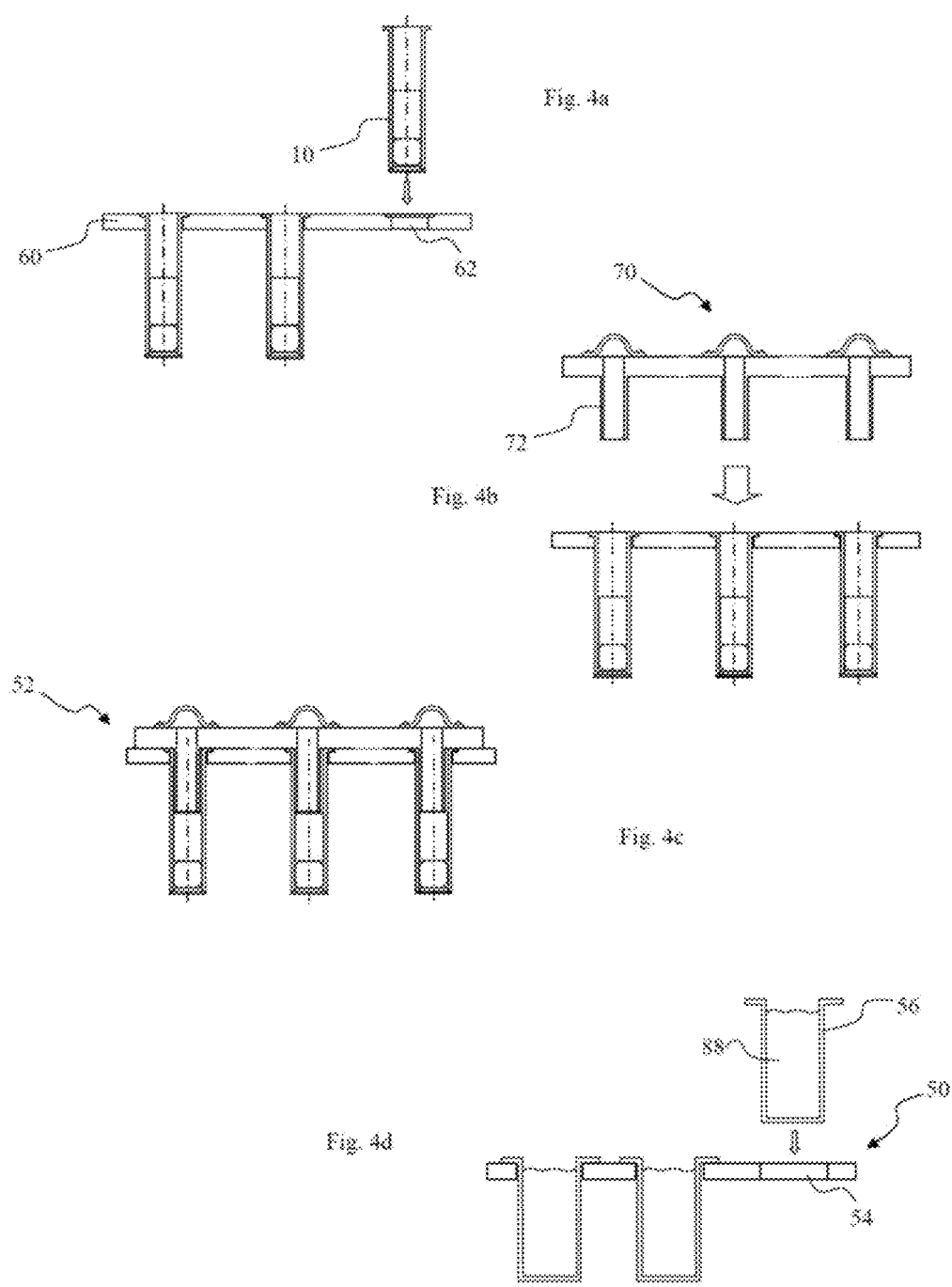

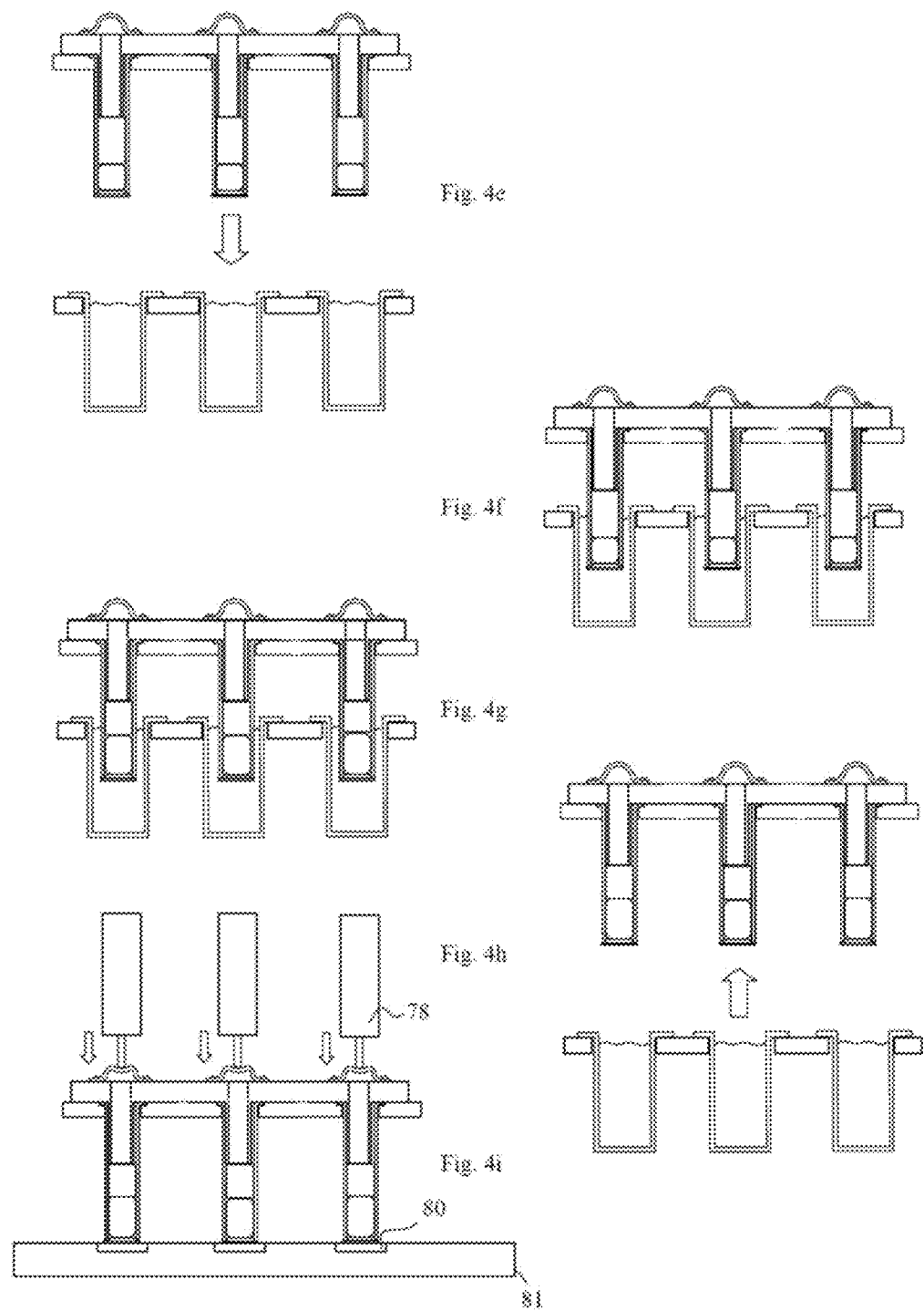

DEVICE FOR CAPTURING BIOLOGICAL PARTICLES

TECHNICAL FIELD

The invention relates to the field concerning the analysis of biological preparations medical diagnostic purposes. More precisely, it relates to a device for capturing biological particles, in particular cells, suspended in a liquid medium, in particular in a biological sample.

The invention also relates to a method for capturing such biological particles, and to an apparatus allowing this method to be carried out.

PRIOR ART

A device for capturing biological particles is described in WO 2010/012941. This device has a tube closed by a filter membrane. An absorbent block is placed inside the tube. When the tube is immersed in a liquid medium, the absorption of water by the absorbent block makes it possible to control the flow entering the tube through the filter membrane. Biological particles are then retained on the filter membrane.

The filter membrane is then applied to a slide, and an output flow is produced through the filter membrane so as to transfer a sample of cells, initially retained on the outer surface of the filter membrane, onto said slide. The cell layer transferred onto the slide advantageously allows a reliable cytological analysis to be performed.

Cytological analysis permits in particular the detection of modifications that are at the origin of, or are associated with, potentially life-threatening diseases, in particular the detection of cancerous or pre-cancerous states such as cancer of the breast, of the urinary tract, of the uterus, etc.

The control of the flow entering through the filter membrane makes it possible to retain a sufficient number of cells to obtain a cell sample that is statistically representative of the cell population in the liquid medium. It also avoids obtaining, on the filter membrane, a number of cells that is too high, which would lead to a cell sample in which the cells form clusters and/or stacks, that is to say a sample from which the subsequent cytological analysis would not be optimal. In particular, when the cells form clusters and/or stacks, there is a significant risk of the cells of interest being unavailable for cytological analysis.

There is a continuing need to further improve the reliability of the capture of cells.

An object of the invention is to respond to this need.

SUMMARY OF THE INVENTION

According to the invention, this object is achieved by means of a device for capturing biological particles in suspension in a liquid medium, the device having:
- a container that is open via a lower opening, preferably a tube of axis X that is open, preferably along the axis X, at upper and lower ends, via lower and upper openings, respectively;
- a filter membrane fixed to the container in such a way as to close the lower opening; and
- inside the container:
  - a buffer made of a porous foam and having a planar face resting on the filter membrane;
  - an absorbent block resting on the buffer and able to absorb said liquid medium when it is in contact with said liquid medium, preferably able to swell under the effect of contact with said liquid medium, and being preferably hydrophilic; and
  - a spring impeding the expansion and/or movement of the absorbent block away from the lower opening of the container, and in particular toward an upper end of the container, especially when the container is said tube.

Surprisingly, the inventor has found that placing such a buffer between the absorbent block and the filter membrane markedly improves the uniformity of the layer of biological particles retained on said filter membrane. Transferring these biological particles to an analysis substrate, for example a slide, advantageously results in a more homogeneous sample, which leads to more reliable analysis.

Without being bound by a theory, the inventor explains this result by the ability of the foam of the buffer to deform in order to compensate for the deformation of the absorbent block. This deformation does not therefore substantially change the distribution of the pressure exerted on the face of the buffer bearing on the filter membrane, which remains uniform over the entire region in which the buffer bears on the filter membrane.

A capture device according to the invention preferably has one or more of the following optional features:
- the thickness of the buffer, measured along the axis X, is greater than 1 mm and less than 4 mm;
- the material of the buffer is preferably polyurethane;
- the buffer has a lower face with a shape complementary to the upper face of the filter membrane;
- the buffer is in contact with more than 80% of an upper face of the filter membrane;
- the device preferably has a limit stop impeding the movement of the spring away from the lower opening of the container, and in particular, when the container is said tube, toward the upper opening of the tube;
- the spring is a block of elastic foam;
- the foam block is shaped in such a way that, in a position in which it is housed inside the container, it is compressed by the side wall of the container;
- the average pore size of the filter membrane is greater than one micron and; or less than 25 microns, and/or the absorbent block is made of a hydrophilic material;
- the container is a tube of axis X opening out at lower and upper ends via lower and upper openings, respectively;
- the difference between the greatest transverse dimensions of the upper opening of the tube, on the one hand, and of the buffer, on the other hand, is greater than 0.2 mm and less than 4 mm.

The invention also relates to a method for capturing biological particles in suspension in a liquid medium, by means of a capture device according to the invention, said method having the following steps:

i) immersing the filter membrane of the container in the liquid medium, the upper end of said container preferably being kept above the surface of the liquid medium;

ii) maintaining the container in position (in the at least partially immersed position obtained at the end of step i)), in a stationary position, or preferably oscillating about the axis X when the container is said tube, in order to bring the biological particles in homogeneous suspension in the liquid, for a duration that is sufficient to retain, on the filter membrane, particles contained in the flow of liquid medium entering the container and generated by the absorption of said liquid medium by the absorbent block;

iii) withdrawing the container from the liquid medium and, optionally, applying the filter membrane to an analysis substrate.

The invention also relates to an analysis apparatus having:
a vial rack;
a container support of capture devices according to the invention; preferably, a finger holder;
preferably, an analysis substrate rack;
a mechanism configured to:
  introduce fingers of the finger holder, when the analysis apparatus has a finger holder, into containers of capture devices according to the invention that are each arranged on the container support, in such a way as to form a container rack,
  introduce the filter membranes the containers arranged on the container support into respective vials arranged on the vial rack, and withdraw said containers from said respective vials, and
  preferably apply the filter membranes of the containers to respective analysis substrates, preferably arranged on the analysis substrate rack.

An analysis apparatus according to the invention preferably has one or more of the following optional features:
  when the analysis apparatus has a finger holder, each finger is preferably pierced with a lumen, said lumen opening out via lower and upper openings that are in fluidic communication respectively with the internal volume of a respective container, after formation of the container rack, and with the internal volume of a bellows, respectively;
  the analysis apparatus having an actuator configured in such a way as to selectively press said bellows in order to increase the pressure inside said container;
  after formation of the container rack, each finger has a lower end in contact with a spring of said capture device.

The invention also relates to a method for preparing a sample intended for biological analysis, in particular cytological analysis, said method having the following steps:
  a) obtaining at least one vial containing a liquid medium containing biological particles, and preferably arranging said vial in a vial rack;
  b) preferably, independently of step a), arranging a capture device according to the invention on a container support;
  c) after step b), when the analysis apparatus has at least one finger, introducing said finger, preferably a finger of a finger holder, through an upper opening of the container of the device, the finger preferably being configured in such a way, that, in the position of maximum introduction of the finger into the container, the buffer contained in the container is in contact with the filter membrane fixed to said container;
  d) introducing the filter membrane of the container into said vial and maintaining the container in position for a duration that is sufficient for the absorbent block to absorb said liquid medium entering the interior of the container through the filter membrane;
  e) withdrawing the container from the vial;
  f) recovering biological particles retained on the filter membrane, preferably by applying the filter membrane to an analysis substrate after a waiting period of over 5 seconds, then preferably increasing the pressure inside the container in such a way as to create a flow of liquid medium exiting the container through the filter membrane.

The preparation method may in particular be carried out using an analysis apparatus according to the invention.

Definitions

In the general context in which the capture device has a "container", the adjectives "upper" and "lower" are not limiting. In the context in which the container is a tube of axis X, they are defined with reference to a position of a device in which the axis X of the tube is substantially vertical (as in FIG. 1). Unless indicated otherwise, "axial" refers to the axis X of the tube.

Unless indicated otherwise, "transverse" means an orientation perpendicular to the axis X of the tube.

The term "biological particles" signifies a particle not soluble in an aqueous liquid medium and susceptible of being contained in a biological material taken from a body of a living multicellular organism, either animal or plant, in particular a multicellular living animal organism, in particular a mammal, including humans. Examples of biological particles include tissue microfragments, microorganisms, living cells, dead cells, a nucleate cell bodies such as erythrocytes and platelets (thrombocytes), fragments, cell debris, and possible crystals, and light solid foreign bodies. Insoluble protein substances, such as pectin, or protein substances derived from fibronectin, for example protein substances derived from fetal fibronectin, which represent a clinical parameter indicative of a risk of premature delivery, are other examples of biological particles.

The "swelling capacity" of an absorbent block is the ratio between the volume of this block after maximum swelling by absorption of liquid medium and its initial dry volume.

Unless indicated otherwise, the verbs "have", "comprise" or "include" must be interpreted broadly and in a non-limiting sense.

BRIEF DESCRIPTION OF THE FIGURES

Other features and advantages of the invention will become clear from reading the following detailed description and from examination of the accompanying drawing, in which:

FIG. 4 (4a-4i) schematically illustrates the different steps of a preparation method according to the invention, in an embodiment using an analysis apparatus according to the invention;

DETAILED DESCRIPTION

Figure 1:
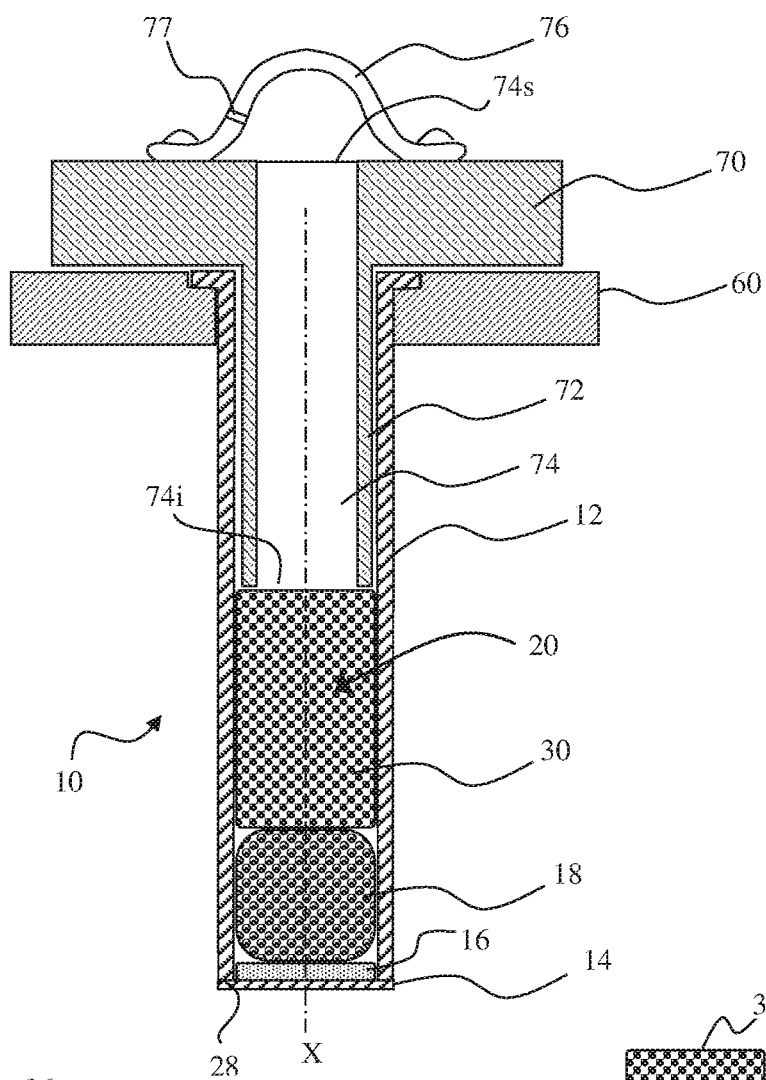
FIG. 1 shows an example of a capture device according to the invention, in a median longitudinal sectional plane.
Figure 2:
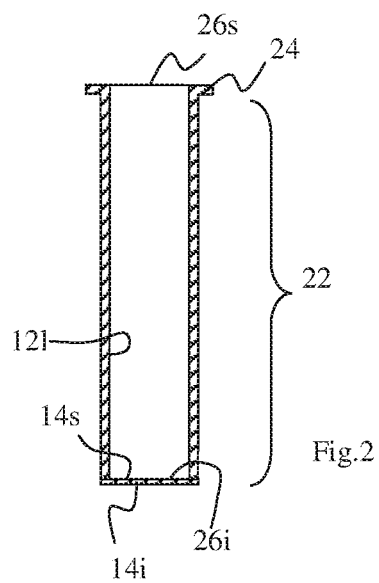
FIGS. 2 and 3 show details of FIG. 1.
Figure 3:
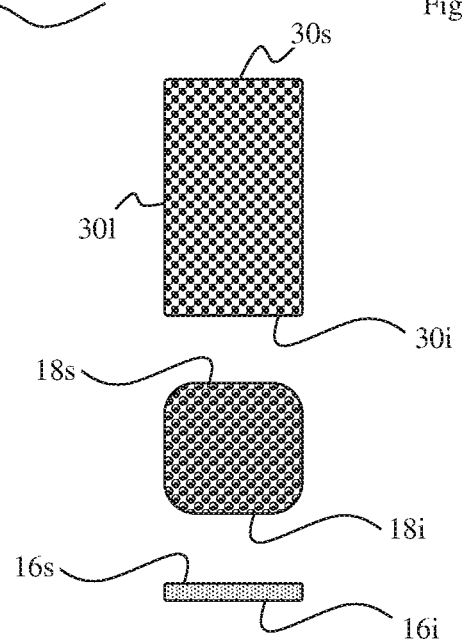

FIG. 1 shows a capture device 10 having a container in the form of a tube 12 of axis X, a filter membrane 14, a buffer 16, an absorbent block 18 and a spring 20.

Tube

The tube 12 has a cylindrical portion 22, preferably of circular cross section, terminated at the upper end of the tube 12 by a flange 24, which is preferably annular.

In a preferred embodiment, the flange 24 is interrupted, thereby defining lugs.

The length of the tube is preferably greater than 5 cm, and/or less than 10 cm. The greatest transverse dimension of the cylindrical portion 22 is preferably greater than 1 cm and/or less than 4 cm.

The thickness of the side wall defining the cylindrical portion 22 is preferably greater than 1 mm and/or less than 5 mm, preferably less than 3 mm.

The tube 12 opens out, at its upper and lower ends, via upper and lower openings, labeled 26s and 26i respectively.

The tube is preferably made of plastic, for example polyvinyl chloride, polystyrene or polyethylene.

The tube 12 may have one or more of the features of the tube labeled "101" as described in WO 2010/012941.

The tube may be of the type commonly used in automated systems for processing biological samples for cytologic analysis.

Filter Membrane

The filter membrane 14 is fixed on the edge 28 of the tube 12 defining the lower opening 26i, in such a way as to completely close said lower opening. Preferably, the filter membrane is adhesively bonded, laser welded or heat-sealed to said edge.

All filter membranes known for cell filtration in the field of cytology, in particular filter membranes made of polyester or polycarbonate, for example the filter membranes sold by the company MILLIPORE (Billerica, Mass., USA) or by the company WHATAM GE HEALTHCARE (Versailles, France), may be used.

A filter membrane from the company IT4IP (Belgium) may also be used.

The average pore size of the filter membrane is adapted to the intended use. Preferably, the average pore size of the filter membrane is greater than one micron, than 3 µm, or greater than 5 µm, and/or less than 200 microns, less than 150 microns, less than 100 microns, less than 50 microns, or less than 25 microns.

In one embodiment, it is greater than 1.5 microns and/or less than 2.5 microns, preferably about 2 microns. The filter membrane may in particular be the membrane designated 7060-2511 as sold by the company WHATAM GE HEALTHCARE. Advantageously, all of the biological particles of interest for a cytological analysis may be sampled by means of such a filter membrane, whatever the nature or tissue origin of the liquid medium.

In another embodiment, the filter membrane has an average pore size of greater than 3 µm, preferably greater than 5 µm and/or less than 10 µm, preferably less than 8 µm, preferably less than 7 µm. The filter membrane may then in particular be a filter membrane designated TMTT-02500 as sold by MILLIPORE, or designated TTT-B02500 as sold by MILLIPORE, or a filter membrane Cyclopore® PC such as the 5 µm membranes designated 7060-2513 or 7060-4713, the 8 µm membranes designated 7060-2514 or 7060-4714 or the 10 µm membranes designated 7060-2515 or 7060-4715. Such membranes may in particular be used to retain only cells of larger sizes, for example epithelial cells resulting from a cervico-vaginal samples or smear.

Buffer

The buffer 16, also called an "adapter buffer", is preferably made of a foam permeable to the liquid medium. Therefore, the liquid medium entering the tube through the filter membrane may quickly reach the absorbent block.

The buffer 16 has an open porosity making it easier for the liquid medium to pass through it.

Preferably, the buffer is configured in such a way that its volume remains substantially constant when it is in contact with water, and more generally with the liquid that has passed through the filter membrane.

Preferably, the buffer 16 has a lower face 16i with a shape substantially complementary to the upper face 14s of the filter membrane 14. Preferably, the faces 16i and 14s are substantially planar, preferably substantially transverse.

Preferably, the buffer 16 is in contact with more than 80%, preferably more than 90%, preferably more than 95%, preferably substantially 100% of the upper face 14s of the filter membrane 14 (exposed to the interior the tube 12).

Preferably, the buffer 16 has a cylindrical shape of axis X. Preferably, the side surface of the buffer 16 substantially complements the inner surface 121 of the tube 12.

Preferably, the buffer has dimensions adapted such that it may be moved freely in the tube. This makes the device easier to assemble.

Advantageously, during assembly, the buffer, introduced through the upper opening of the tube 12, may thus slide by gravity along the tube, until it comes into abutment with the filter membrane.

Preferably, the difference between the greatest transverse dimensions of the upper opening of the tube, on the one hand, and of the buffer, on the other hand, is greater than 0.2 mm, greater than 0.5 mm, preferably greater than 0.8 mm and/or less than 4 mm, preferably less than 3 mm, preferably less than 2.5 mm.

The thickness of the buffer, measured along the axis X, is preferably constant and preferably greater than 1 mm, preferably greater than 1.5 mm and/or preferably less than 4 mm, preferably less than 3 mm, preferably less than 2.5 mm. The best results have been obtained with a thickness of 2 mm.

Absorbent Block

The absorbent block 18 may have one or more of the features of the block of absorbent material described in WO 2010/012941.

Preferably, the absorbent block 18 has a cylindrical shape of axis X, preferably of circular cross section, preferably substantially complementing the inner surface 121 of the tube 12. Preferably, it has dimensions adapted such that it may be moved substantially freely within the tube. This makes the device easier to assemble.

Advantageously, during assembly, the absorbent block, introduced through the upper opening of the tube 12, may thus slide by gravity along the tube, until it comes into abutment with the buffer 16.

Preferably, the difference between the greatest transverse dimensions of the upper opening of the tube, on the one hand, and of the absorbent block, on the other hand, is greater than 0.2 mm, greater than 0.5 mm, preferably greater than 0.8 mm and/or less than 4 mm, preferably less than 3 mm, preferably less than 2.5 mm.

The thickness of the absorbent block, measured in the direction of the axis X, is preferably greater than 5 mm, greater than 8 mm, greater than 9 mm and/or less than 30 mm, less than 20 mm, preferably less than 15 mm, preferably less than 12 mm.

Preferably, the absorbent block 18 has a lower surface 18i with a shape substantially complementing the upper face 16s of the buffer 16. Preferably, the faces 16s and 18i are substantially planar, preferably substantially transverse.

The absorbent block 18 has, or preferably consists of, a material that swells under the effect of contact with a liquid medium.

Preferably, the absorbent pad consists of a hydrophilic material that swells when placed in contact with an aqueous liquid medium, in particular with water. Preferably, this material has, preferably consists of, viscose, preferably compressed viscose. In a preferred embodiment, the absorbent block 18 consists of a stack of viscose sheets, preferably of non-woven viscose sheets, the stack of said sheets having been compressed Viscose has the advantage of having good water absorption, but also of having a good capacity to swell under the effect of this absorption.

Preferably the absorbent block has a swelling capacity of greater than 2, preferably greater than 3, preferably greater than 4. Such a swelling capacity may be obtained in particular with viscose.

The absorbent block 18 may also have, or even consist of, a superabsorbent that is well known to a person skilled in the art, for example of the hydrogel type. The superabsorbent may in particular be a polymer such as crosslinked sodium polyacrylate, which is obtainable by a polymerization reaction of an acrylic acid blended with sodium hydroxide in the presence of a polymerization initiator, a copolymer of polyacrylamide, a copolymer of ethylene maleic anhydride, a crosslinked carboxymethyl cellulose, a copolymer of polyvinyl alcohol or a crosslinked polyethylene oxide.

In one embodiment, the swelling capacity is greater than 10, greater than 15, preferably greater than 20, or even greater than 30. Such a swelling capacity is possible in particular with crosslinked sodium polyacrylate, the swelling capacity of which may reach 60.

Spring

The spring 20, or "spring buffer", has the function of
impeding, without blocking, the expansion of the absorbent block and its movement toward the upper opening of the tube, which limits the deformation of the filter membrane, and
maintaining permanent contact between the absorbent block and the buffer, but also between the buffer and the filter membrane.

The elasticity of the spring is preferably sufficient to compensate for an elongation of the absorbent block, along the axis X, of more than 5%, preferably more than 10%, or even more than 15%.

In a preferred embodiment, the spring 20 has a foam block 30 arranged on the upper face 18s of the absorbent block 18.

The foam block may have the form of a rectangular parallelepiped, for example a cube, of which the greatest dimension may be more than 1 cm, more than 1.5 cm, more than 2 cm and/or less than 4 cm, or less than 3 cm.

The elasticity of the foam block is preferably such that it allows the volume thereof to be reduced by a factor greater than 2, preferably greater than 4, preferably greater than 6, preferably greater than 8, preferably greater than 10, preferably greater than 15, preferably greater than 20, by manual compression, for example between index finger and thumb.

The elasticity and the volume of the foam block are preferably determined such that the deformation of the foam block may compensate elastically for the increase in volume of the absorbent block during its swelling.

The foam of the foam block 30 may be based on polyols and isocyanates. It may be of polyurethane. It may in particular be made of RICHLUX HIGH RESILIENCE HR50065, RG50030 or RG50036, sold by the company CARPENTER BELGIUM NV (Belgium).

To ensure that the spring, in particular the foam, may exert its spring action, its movement toward the upper opening of the tube must be impeded or even blocked. As will be seen in more detail, this impeding of the spring may in particular result from the pressing of a finger inserted into the tube through the upper opening thereof, or from the pressing of the spring against a limit stop of the tube.

The foam block preferably extends within the tube by a height, measured along the axis X, of less than 4 cm, preferably less than 3 cm, preferably less than 2.5 cm.

In one embodiment, the foam block is shaped in such a way as to rub on the inner surface 121 of the side wall of the tube. In one embodiment, the greatest dimension in a cross section of the foam block, measured when the foam block is outside of the tube, is slightly greater than the internal diameter of the tube, for example greater by 0.2 mm, greater by 0.5 mm, or greater by 1 mm than said diameter. Therefore, in order to be introduced into the tube, the foam block has to be slightly compressed laterally. Advantageously, the necessity of having to laterally compress the block of foam for introducing it into the tube facilitates the hold, in the tube, of the buffer 16 and of the absorbent block 18.

Advantageously, the friction of the foam block impedes its movement during expansion of the absorbent block.

In one embodiment, in order to impede the movement of the foam block 30, in addition to or instead of said friction, a limit stop is arranged above the foam block 30. This limit stop may be integrated in the device or may be added at the time when the device is to be used, like the finger described below.

In a preferred embodiment, the foam block 30 has a lower face 30i which is substantially complementary to the upper face 18s of the absorbent block, preferably substantially planar, preferably substantially transverse.

The shape of the foam block 30 is not limited. In particular, the area of the side surface 30l of the foam block 30, which is in contact with the inner surface of the tube 12, is not limited and may be advantageously modified depending on the desired spring action.

The spring 20 may also comprise, or even consist of, elastic means other than a foam block. For example, it may comprise a helical spring of which a lower end bears on the absorbent block 18 and the opposite end is immobilized with respect to the tube, at least temporarily, for example by a limit stop fixed on the tube.

Analysis Apparatus

Figure 7:
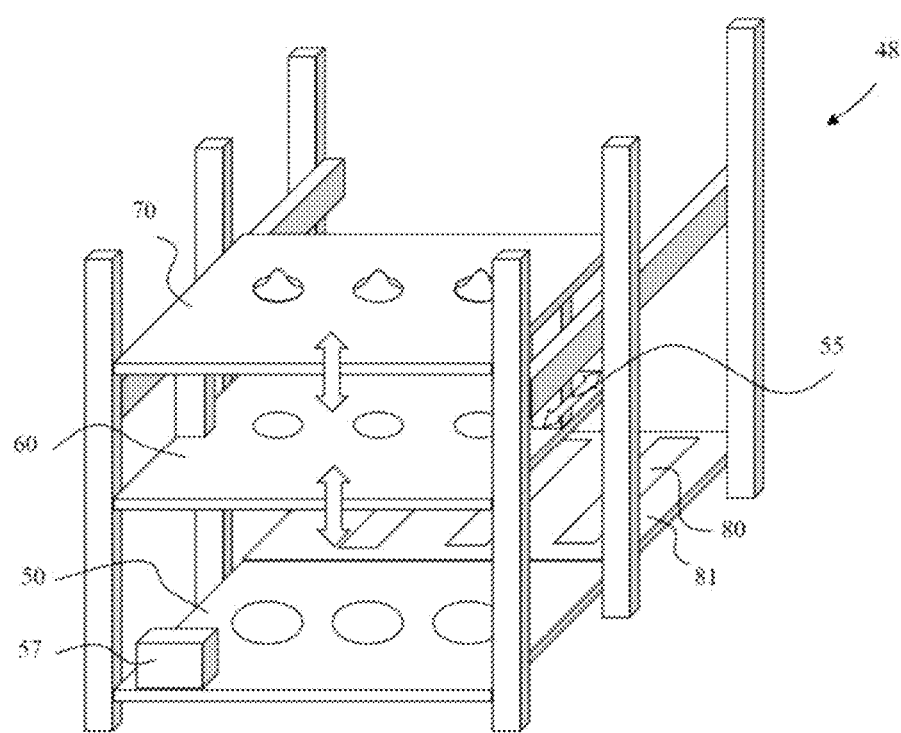
FIG. 7 illustrates schematically an apparatus according to the invention.

A capture device may advantageously be used with an analysis apparatus 48 according to the invention, illustrated in FIG. 7. An analysis apparatus 48 has a vial rack 50, a container rack, in this case a tube rack 52, formed by joining a container support, in this case a tube support 60, and an optional finger holder 70, optionally an analysis substrate rack 81, and a mechanism 55 for moving these various elements relative to one another in order to perform steps a) to f).

The mechanism 55 of the analysis apparatus 48 is not limited, provided that it allows the vial rack 50, the tube support 60, the finger holder 70, then the tube rack 52 resulting from the assembly of the tube support and the finger holder 70, and the analysis substrate rack 81 to be moved relative to one another. The realization of such a mechanism does not pose any particular problems.

Preferably, an apparatus according to the invention furthermore comprises a controller 57 adapted to control the mechanism 55 such that the various steps of the method may be linked together without human intervention.

The vial rack 50 is preferably in the form of a plate pierced with one or more vial orifices 54, each configured to receive a vial 56 containing liquid medium loaded with biological particles to be captured.

The vial rack 50 preferably comprises more than one, preferably more than two, preferably more than five, preferably more than ten vial orifices 54, each adapted to retain a vial 56 in a substantially vertical position. For this purpose, the vial 56 preferably has an annular flange that prevents it from passing through the vial orifice 54 in which it is arranged.

The tube rack 52 preferably comprises a tube support 60, preferably in the form of a plate pierced with one or more tube orifices 62, each configured to receive a capture device according to the invention. In particular, each tube orifice 62 may be shaped so as to allow the cylindrical portion 22 of the tube 12 of a device to pass through, while preventing the passage of the flange 24.

The number of tube orifices 62 of the tube support 60 is preferably identical to the number of vial orifices 54 of the vial rack.

Preferably, the tube rack 52 also has means for immobilizing each capture device on the tube support 60, for example jaws that are rigidly connected to the tube support and clamp the tubes suspended in their respective tube orifices.

The finger holder 70 has one or more fingers 72 or "pushers", which may be introduced into tubes arranged on tube rack.

Preferably, each finger has, externally, the general shape of a substantially rectilinear rod.

The length of a finger is preferably greater than 1 cm, 2 cm or 5 cm.

The fingers protrude from a base 73, for example in the form of a plate, to which they are preferably rigidly fixed. The introduction of all the fingers into the respective tubes, in step c), may thus be advantageously simultaneous.

The finger holder 70 has as many fingers as there are tube orifices 62 on the tube support 60. After introduction of a finger into a tube, as shown in FIG. 4c, the finger extends substantially along the axis X.

Preferably, each finger 72 is pierced with a longitudinal lumen 74 which opens out, via lower 74l and upper 74s openings, to the foam block 30 and into the internal volume of a bellows 76. The operation of the bellows, that is to say its compression for reducing its volume, therefore makes it possible for the gas contained in the bellows, preferably air, to be injected into the inside of the longitudinal lumen 74 and thus to the foam block 30.

In the position of maximum introduction of a finger 72 into a tube 12, as shown in FIG. 1, the lower end of the finger is preferably in contact with the upper face 30s of the foam block 30, in a position which ensures that the buffer is in contact with the filter membrane.

Before use of the capture device, the various components inside the tube may in fact have been able to move, for example during their transport. If these components are no longer in the service position shown in FIG. 1, introduction of the finger pushes them back toward the filter membrane until the foam block is in contact with the absorbent block, the absorbent block in contact with the buffer, and the buffer in contact with the filter membrane (FIG. 1).

Advantageously, the finger 72 may also serve as a limit stop for limiting the movement of the foam block 30 toward the upper opening of the tube during the expansion of the absorbent block.

Preferably, the bellows 76 is provided with a vent 77 permitting limited release of air when a pressure is exerted on the bellows 76 in order to reduce the internal volume thereof. The vent 77 also means that atmospheric pressure may at all times be maintained inside the tube 12 during the swelling of the absorbent block 18.

The bellows, which preferably has the form of a nipple or suction cup, is preferably fixed on the finger holder, and preferably on the upper surface of the finger holder 70, for example by means of rivets.

Operation

The operation of the capture device according to the invention is described in the context of the preparation method according to the invention.

Step a) is illustrated in FIG. 4d.

The vial 56 may in particular be a vial commonly used for the packaging of cell samples or tissue samples for biological analyses, including cytological or histological analyses.

The liquid medium 88 contained in the vial may consist of a buffered aqueous liquid medium containing an agent for fixing the cells or cell bodies in suspension. As fixing agents, mention may be made in particular of alcohol-based mixtures, for example the agent sold under the trade name SEDFIX® by the company SURGIPATH, or the one sold under the trade name PRESERVCYT® by the company HOLOGIC, or the one sold under the trade name EASYFIX® by the company VWR. In particular, when the cytological analysis has to be performed on living cells, the liquid medium may consist of a buffered saline medium, preferably a suitable cell culture medium. The liquid medium may also consist of a natural body fluid such as blood or urine, or any natural or pathological physiological secretion such as ascites, effusions, a cyst or another flow.

In step b), the tubes of a set of capture devices 10 according to the invention are arranged in the tube orifices 62 of a tube support 60, as illustrated in FIG. 4a. The capture devices are at least arranged in the tube orifices 62 which, when the tube rack and vial rack are brought together, will be facing the vials arranged in the vial orifices, as shown in FIG. 4e.

In step c), the fingers are arranged opposite the tube orifices 62 so as to be able to be introduced into the tubes of the capture devices arranged in the tube orifices 62, as shown in FIG. 4b.

The fingers 72 are then each introduced into a corresponding tube (FIG. 4b) until the finger holder comes into abutment on the tube support 60. The assembly formed by the tube support 60 and the finger holder 70 constitutes a tube rack 52 which, preferably, is not disconnected again until the end of the last step of the method (FIG. 4c).

In step d), the tube rack is arranged in such a way that the tubes that it holds are opposite the upper openings of the vials 56 in order to be able to be introduced into said vials (FIG. 4e). The depth of penetration of the tubes into the vials is determined in such a way that the filter membrane 14, the buffer 16 and at least a part of the absorbent block 18 of each tube are below the upper surface of the liquid medium contained in the vials 56. By hydrostatic pressure, liquid medium thus penetrates inside the tube, through the filter wall 14, and then wets the absorbent block 18.

The apparatus illustrated is provided for simultaneous processing of three sample vials. However, the operation of the apparatus is the same whatever the vial in question. In the following description, this operation is therefore described only for a single vial.

As illustrated in FIGS. 4*f* and 4*g*, the absorbent block 18 contained in the tube introduced into this vial absorbs some of the liquid medium having penetrated into the tube 12 and swells. In particular, the swelling of the absorbent block 18 results in its expansion toward the upper opening of the tube, against the foam block 30, and toward the filter membrane 14, against the buffer 16 and the filter membrane 14. The presence of the absorbent block ensures a minimal inward flow, especially through the surface tension force arising from the surface energy characteristics of the absorbent block and the mechanical suction action resulting from the expansion of the absorbent block.

The finger 72 opposes the movement of the foam block 30 to the upper opening of the tube and therefore forces the foam block 30 to contract. The elasticity of the foam block 30 advantageously allows the absorbent block 18 to be maintained against the buffer 16, and the buffer 16 against the filter membrane 14.

The buffer 16 allows a good distribution of the pressure exerted by the absorbent block 18 and ensures a substantially homogeneous inward flow through the filter membrane 14.

During the passage of the liquid medium through the filter membrane 14, the biological particles are retained on the lower face 14*i* of the filter membrane 14. The uniformity of the flow of the liquid medium through the filter membrane advantageously ensures a homogeneous distribution of the biological particles on the lower face 14.

The tube is maintained in the vial for a determined duration depending on the quantity of biological particles to be fixed on the filter membrane 14 (FIG. 4*g*). The partially immersed position is preferably maintained for more than 5 seconds and/or less than 10 minutes. Preferably, this duration is adapted to the nature of the liquid medium, and in particular to the concentration of the biological particles in the liquid medium, the desired density of the biological particles on the filter membrane, and the absorption capacity of the absorbent block.

The tube rack is then moved away from the vial rack, as shown in FIG. 4*h*, so as to completely remove the tube from the vial.

The biological particles are then recovered in order to form a sample that is adapted to be observed, especially in order to perform a cytological analysis.

In a preferred embodiment, the lower surface 14*i* of the filter membrane is applied to an analysis substrate 80, as shown in FIG. 4*i*.

Prior to this application, the tube is preferably kept outside the vial, and without contact with the analysis substrate, for a waiting period of preferably more than 5 seconds, preferably more than 30 seconds, preferably more than 1 minute, and preferably less than 5 minutes, preferably less than 3 minutes, preferably less than 2 minutes. This waiting period is preferably determined such that the absorbent block absorbs the residual liquid medium which is present in the tube and is "free", that is to say which is not contained in the buffer or in the absorbent block.

The analysis substrate 80 may in particular be a glass slide.

Preferably, the analysis substrate 80 is arranged on a substrate rack 81, the substrate rack preferably being configured to receive as many analysis substrates as the tube support 60 may receive tubes.

Preferably, the analysis apparatus comprises means for generating a flow of liquid medium exiting the tubes when the filter membranes are applied to respective analysis substrates.

Specifically, a pressure is applied to the bellows 76 (arrows in FIG. 4*i*) in order to exert an overpressure of short duration. Preferably, the deformation of the bellows is effected by means of an actuator 78 in the form of a thrustor, of which the rod bears rapidly on said bellows. This overpressure creates a flow of liquid medium out of the tube, through the filter membrane 14, which causes the biological particles to detach from this membrane. The biological particles thus detached are transferred to the analysis substrate 80.

Preferably, when the actuator rod retracts, the bellows elastically recovers its initial shape.

This method of transferring biological particles by replica plating of the filter membrane is a method conventionally used by anatomopathologists.

Other transfer methods are possible. In particular, the filter membrane may simply be pressed against the analysis substrate.

The sample may then be subjected to one or more processing steps before undergoing observation, for example one or more steps involving specific or nonspecific staining, including May-Grünwald. Giemsa staining, "Papanicolau" staining, Shorr staining, hematoxylin, eosin, etc.

Prior to their observation, the transferred biological particles may also undergo an incubation step in the presence of specific detectable antibodies of membrane markers or intracellular markers, and/or treatment by a molecular biochemistry technique, for example by in situ hybridization with specific nucleic acid probes or an RNA extraction technique and quantification of the level of expression of one or more genes of interest, or a DNA extraction technique and detection of mutation in the sequence of one or more genes of interest.

In one embodiment, the filter membrane 14 is detached, and the filter membrane and the retained biological particles are included in paraffin or a suitable resin, which is particularly useful for recovering tissue microfragments for analysis purposes, in particular for producing histological sections.

The embodiment of the capture device illustrated in FIGS. 1 and 4 is particularly well suited to automation.

However, the invention is not limited to this embodiment.

Figure 5:
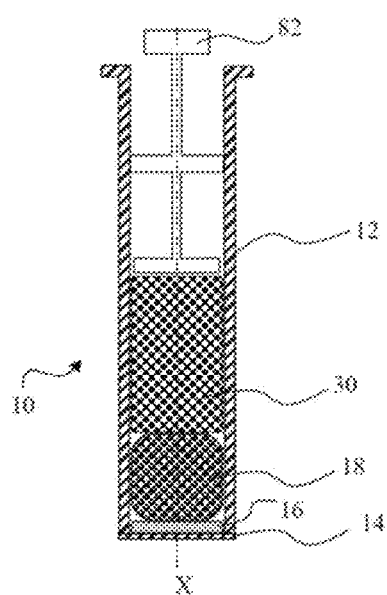
FIGS. 5 and 6 show second and third specific embodiments of a capture device according to the invention.

In particular, as shown in FIG. 5, the capture device may comprise a piston 82, which replaces the finger 72 and the actuator 78. All steps may be performed manually, the piston being operable by hand.

Thus, in the embodiment of FIG. 5, the capture device advantageously comprises means for manually detaching the biological particles from the filter membrane 14.

The piston 82 may in particular have one or more of the optional features of the piston "104" described in WO 2010/012941. As described in WO 2010/012941, the upper opening of the tube 12 may also be closed by a plug having an orifice for guiding the sliding movement of the piston 82 in the tube.

Figure 6:
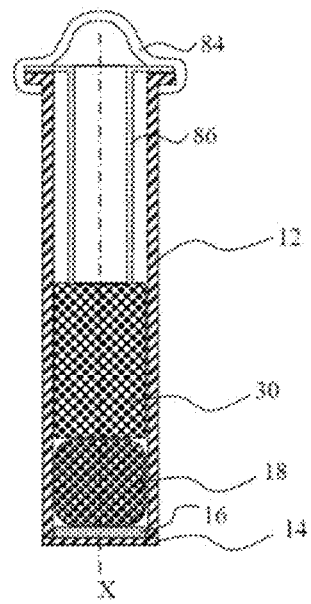

In the embodiment of FIG. 6, the piston is replaced by a bellows 84 which is similar to the bellows 76 and which operates in an identical manner. However, the bellows 84 is fixed to the upper edge of the tube.

In addition, a limit stop is provided in order to block the foam block 30. The shape of this limit stop is not limiting. For example, it may be formed by an inner tube 86 housed in the tube 12, similar to the finger pin 72, preferably immobilized with respect to the tube. An upper flange 88 of the inner tube 86 may, for example, be sandwiched between the bellows 84 and the tube 12, as shown.

The capture device is thus autonomous and may be used by hand.

As will be clear now, the invention makes available a capture device which, by virtue of the presence of the buffer 16, promotes a homogeneous distribution of the biological particles retained on the filter membrane 14.

The reliability of the analyses performed using these biological particles is thereby improved.

Furthermore, the invention makes available an analysis apparatus permitting automation of the various steps of the method for preparing an observable sample, especially for cytological analysis. This apparatus advantageously makes it possible to multiply the measurements performed.

Of course, the invention is not limited to the embodiments described in detail and/or illustrated, these being provided for illustrative purposes only. In particular, the container is not limited to a tube. All of the features described above for a tube may therefore be applied to another form of container, except those ones that are specific to a tubular shape. The filter membrane is not necessarily fixed to a lower end of the container, although this is preferred.

The container may have any dimensions and any structure, provided that it is shaped such that the spring impedes the expansion and/or movement of the absorbent block.

In one embodiment, the spring may be integrated in the wall of the container, the wall of the container preferably being elastically deformable in order to impede the expansion and/or movement of the absorbent block. For example, all or part of the wall of the container may be formed by an elastically deformable film which is tensioned in order to exert an elastic pressure on the absorbent block.

In one embodiment, the container does not have an upper opening. The wall of the container then defines, with the filter membrane, a closed chamber which preferably communicates with the outside only by way of the filter membrane.

The wall of the container may be rigid or flexible.

Finally, the invention is not limited to a particular field of application. It may also be used, for example, for investigation of legionellosis.

The invention claimed is:

1. A device for capturing biological particles in suspension in a liquid medium, the device having:
   a container that is open via a lower opening;
   a filter membrane fixed on the container in such a way as to close the lower opening; and
   inside the container:
      a buffer made of a porous foam and having a planar lower face resting on the filter membrane;
      an absorbent block resting on the buffer and able to absorb said liquid medium when it is in contact with said liquid medium; and
      a spring designed to impede the expansion and/or movement of the absorbent block away from the lower opening of the container.

2. The device as claimed in claim 1, in which the thickness of the buffer, measured along the axis X, is greater than 1 mm and less than 4 mm.

3. The device as claimed in claim 1, in which the buffer is made of polyurethane.

4. The device as claimed in claim 1, in which the planar lower face of the buffer has a shape complementary to an upper face of the filter membrane.

5. The device as claimed in claim 1, in which the buffer is in contact with more than 80% of an upper face of the filter membrane.

6. The device as claimed in claim 1, having a limit stop impeding the movement of the spring away from the lower opening of the container.

7. The device as claimed in claim 1, in which the spring is a block of elastic foam.

8. The device as claimed in claim 7, in which said block is shaped in such a way that, in a position in which it is housed inside the container, it is compressed by the wall of the container.

9. The device as claimed in claim 1, in which the average pore size of the filter membrane is greater than one micron and/or less than 25 microns, and/or the absorbent block is made of a hydrophilic material.

10. The device as claimed in claim 1, in which the container is a tube of axis X opening out at lower and upper ends via lower and upper openings, respectively, the spring being able to impede the expansion and/or movement of the absorbent block toward the upper end of the tube.

11. The device as claimed in claim 10, in which the difference between
   a greatest transverse dimension of the upper opening of the tube, and
   a greatest transverse dimension of the buffer is greater than 0.2 mm and less than 4 mm.

12. A method for capturing biological particles in suspension in a liquid medium, by means of a capture device as claimed in claim 1, said method having the following steps:
   i) immersing the filter membrane of the container of said capture device in the liquid medium;
   ii) maintaining the container in position for a duration that is sufficient to retain, on the filter membrane of said capture device, particles contained in a flow of liquid medium entering the container and generated by the absorption of said liquid medium by the absorbent block of said capture device;
   iii) withdrawing the container from the liquid medium and, optionally, applying the filter membrane to an analysis substrate.

13. The method as claimed in claim 12, in which the container is a tube of axis X, opening out at lower and upper ends via lower and upper openings, respectively, and in which, in step i), the lower end of the tube is immersed in the liquid medium, the upper end of said tube being kept above the surface of the liquid medium.

14. An analysis apparatus having:
   a vial rack;
   a container support;
   a finger holder having fingers;
   capture devices as claimed in claim 1;
   optionally, a rack of analysis substrates;
   a mechanism configured to:
      introduce the fingers of the finger holder into containers of said capture devices, each of said containers opening out, at lower and upper ends, via lower and uppers openings, respectively, and being arranged on the container support, in such a way as to constitute a container rack, each finger having a lower end which, after formation of the container rack, is in contact with a spring of a respective capture device among said captures devices, in such a way that said spring is in contact with the absorbent block of said respective capture device, said absorbent block is in contact with the buffer of said respective capture device, and said buffer is in contact with the filter membrane of said respective capture device, introduce said containers, arranged on the container support, into respective vials arranged on the vial rack, or withdraw said containers from said respective vials, and, optionally, apply the filter membranes of said containers to respective analysis substrates.

15. The analysis apparatus as claimed in claim 14, having a set of bellows, and in which each finger is pierced with a lumen, said lumen opening out via lumen lower and lumen upper openings that are in fluidic communication respectively with the internal volume of a respective container, after formation of the container rack, and with the internal volume of a respective bellows.

16. The analysis apparatus as claimed in claim 15, having an actuator configured in such a way as to selectively press said bellows in order to increase the pressure inside said container.

17. A method for preparing a sample intended for biological analysis, in particular cytological analysis, said method having the following steps:

a) obtaining at least one vial containing a liquid medium containing biological particles, and arranging said vial in a vial rack of an analysis apparatus as claimed in claim 14;

b) introducing a finger of a finger holder of said analysis apparatus through an upper opening of a container of one of said capture devices, the finger being configured in such a way that, in a position of maximum introduction of the finger into the container, the buffer contained in the container is in contact with the filter membrane fixed on said container;

c) introducing the filter membrane of the container into said vial and maintaining the container in position for a duration that is sufficient for the absorbent block of the capture device to absorb said liquid medium entering the interior of the container through the filter membrane of the capture device;

d) withdrawing the container from the vial;

e) recovering biological particles retained on the filter membrane by:

holding the container out of the vial for a waiting period of more than 5 seconds, then applying the filter membrane to an analysis substrate arranged on an analysis substrate rack of the analysis apparatus, then increasing the pressure inside the container in such a way as to create a flow of liquid medium exiting the container through the filter membrane.

* * * * *